US012382973B2

(12) United States Patent
Rascon (10) Patent No.: US 12,382,973 B2
(45) Date of Patent: Aug. 12, 2025

(54) METHOD FOR PREPARING A LIQUID OAT BASE AND PRODUCTS PREPARED BY THE METHOD (71) Applicant: Glucanova AB, Lund (SE)

(72) Inventor: Ana Rascon, Lund (SE)

(73) Assignee: Glucanova AB, Lund (SE)

( * ) Notice: Subject to any disclaimer, the term of this patent is extended or adjusted under 35 U.S.C. 154(b) by 379 days.

(21) Appl. No.: 16/225,061

(22) Filed: Dec. 19, 2018

(65) Prior Publication Data
US 2019/0191730 A1 Jun. 27, 2019

Related U.S. Application Data (62) Division of application No. 14/787,295, filed as application No. PCT/EP2014/054083 on Mar. 3, 2014, now abandoned.

(30) Foreign Application Priority Data

Apr. 30, 2013 (SE) .................... 1300314-0

(51) Int. Cl.
A23C 9/13 (2006.01)
A23L 7/10 (2016.01)
(Continued)

(52) U.S. Cl.
CPC ............ *A23C 9/1315* (2013.01); *A23L 7/107* (2016.08); *A23L 7/115* (2016.08); *A23L 33/21* (2016.08);
(Continued)

(58) Field of Classification Search
CPC .................................................... A23C 9/1315
See application file for complete search history.

(56) References Cited

U.S. PATENT DOCUMENTS 3,157,513 A 11/1964 Allen
4,996,063 A 2/1991 Inglett
(Continued)

FOREIGN PATENT DOCUMENTS

WO 2000030457 A1 6/2000
WO WO-0030457 A1 * 6/2000 ............... A23L 2/52
(Continued)

OTHER PUBLICATIONS

"Labcompare" Homogenizers Buyers' Guide _ Labcompare.com 2012 pp. 3-6 https://www.labcompare.com/10-Featured-Articles/119184-Homogenizers-Buyers-Guide/ (Year: 2012).*
(Continued)

Primary Examiner — Felicia C Turner (57) ABSTRACT

In a method of preparing a liquid oat base a material comprising oat bran is suspended in an aqueous media and contacted with α-amylase, β-amylase, β-glucanase, and xylanase to raise the concentration of soluble arabinoxylan by a factor of 5 or more. Also disclosed is a liquid oat base obtainable by the method; a powderous oat base obtained by drying the liquid oat base; uses of the liquid and powderous oat bases and food products comprising them. A powderous composition for use in preparing liquid oat base comprises oat bran, α-amylase, β-amylase, β-glucanase, and xylanase.

19 Claims, 3 Drawing Sheets (51) Int. Cl.
*A23L 7/104* (2016.01)
*A23L 33/21* (2016.01)
*A61K 31/716* (2006.01)

(52) U.S. Cl.
CPC ........ *A61K 31/716* (2013.01); *A23V 2002/00* (2013.01)

(56) References Cited

U.S. PATENT DOCUMENTS

| | | | |
|---|---|---|---|
| 5,525,151 A | 6/1996 | Lenz | |
| 5,792,499 A | 8/1998 | Atwell | |
| 5,874,274 A | 2/1999 | Jakobsen et al. | |
| 6,197,952 B1 * | 3/2001 | Fox | C08B 37/0024 536/127 |
| 6,323,338 B1 * | 11/2001 | Potter | C08B 37/0003 424/401 |
| 6,451,369 B1 | 9/2002 | Triantafyllou | |
| 6,558,930 B2 | 5/2003 | Hwang et al. | |
| 7,910,143 B2 | 3/2011 | Kvist et al. | |
| 7,977,319 B1 | 7/2011 | Levine | |
| 2002/0037331 A1 * | 3/2002 | Hwang | A23L 7/115 536/123 |
| 2002/0094357 A1 | 7/2002 | Aloise | |
| 2004/0197848 A1 | 10/2004 | Behun et al. | |
| 2004/0258829 A1 * | 12/2004 | Zheng | A23L 7/126 426/615 |
| 2005/0089602 A1 | 4/2005 | Kvist | |
| 2008/0241337 A1 | 10/2008 | Durand | |
| 2010/0098805 A1 | 4/2010 | Vykhodtsev | |
| 2011/0020523 A1 | 1/2011 | Pereyra | |
| 2011/0143401 A1 | 6/2011 | De Laat et al. | |
| 2011/0143402 A1 | 6/2011 | De Laat et al. | |
| 2011/0274786 A1 | 11/2011 | Sorensen | |
| 2012/0034341 A1 | 2/2012 | Chen et al. | |
| 2013/0183405 A1 | 7/2013 | Chatel | |
| 2014/0356922 A1 | 12/2014 | Cramer | |

FOREIGN PATENT DOCUMENTS

| | | | |
|---|---|---|---|
| WO | 2001067891 A1 | 9/2001 | |
| WO | 2004086878 A2 | 10/2004 | |
| WO | WO-2004099257 A1 * | 11/2004 | .......... A23K 20/163 |
| WO | 2010081870 A1 | 7/2010 | |
| WO | 2013173869 A1 | 11/2013 | |

OTHER PUBLICATIONS

Cleary et al. "Assessing mixing characteristics of particle-mixing and granulation devices" Particuology vol. 2008 pp. 419-444 (Year: 2008).*

Johansson et al.; Structural characterization of water soluable B-glucan of Oat Bran; Carbohydr Polym 42 (2002).

Tyle P.; Effect of size, shape and hardness of particles in particles in suspension of oral texture and palatability; Acta Physiologica 84 (1993) 111-18.

International Search Report for PCT/EP2014/054083, ISA/EP, Rijswijk, NL, mailed May 22, 2014.

Office Action dated Dec. 19, 2017 in corresponding JP Application 2016-510967, translation, six pages.

Tian, et al.; Characterization of (Glucurono)arabinoxylans from Oats Using Enzymatic Fingerprinting; Journal of Agricultural and Food Chemistry; DOI: 10.1021/acs.jafc.5b04419 J. Agric. Food Chem. 2015, 63, 10822?10830; ACS Publications, Dec. 4, 2015.

* cited by examiner

METHOD FOR PREPARING A LIQUID OAT BASE AND PRODUCTS PREPARED BY THE METHOD

FIELD OF THE INVENTION

The present invention relates to a method of preparing a liquid oat base for use in the manufacture of food for human consumption, to products prepared by the method and their use.

BACKGROUND OF THE INVENTION

Oat bran is the cell wall layer enclosing the oat endosperm and germ from which it can be separated by milling techniques. In addition to cellulose, starch and pectin, oat bran is rich in cell wall polysaccharides of two kinds, β-glucan and arabinoxylan.

β-Glucan is a high molecular weight linear polysaccharide comprising about 70% 1-4—O— and 30% 1-3—O— linked β-D-glucopyranosyl units. Native β-glucan has a molecular weight in the order of $1-2 \times 10^6$ Dalton. Most of native oat glucan can be solubilized by treatment at 60° C. with water. In aqueous solution β-glucan can be degraded by treatment with β-D-glucanase, which hydrolyzes 1-β—O glucosidic linkages. An important feature of aqueous solutions of β-glucan is their viscosity.

The pentosan arabinoxylan is a constituent of oat bran. It is a structurally complex hemicellulose comprising (1-4)-β-D-xylopyranosyl chains (xylose chains) to which α-L-arabinofuranosyl (arabinose) and other residues are attached. Water-soluble arabinoxylan also imparts viscosity to the aqueous phase. However, only a small portion of native oat bran arabinoxylan is water soluble. For this and other reasons arabinoxylan is resistant to enzymatic hydrolysis. Internal (endo-β-1,4-xylopyranosyl) linkages in xylan can be hydrolyzed by xylanases (endo-β-1,4-xylanases).

Oat bran, whole groat meal (whole meal), rolled oats, groats or oat endosperm flour is used as a raw material for health foods such as oat fiber drinks. Their positive health effect linked to its β-glucan content is believed to be due to an increase of intestine fluid viscosity, delay of gastric emptying, slowing of intestinal transit and of glucose and sterol absorption (Johansson et al., *Structural characterization of water soluble β-glucan of oat bran*. Carbohydr Polym 42 (2002) 143-148). Oat fiber drinks contain particulate matter.

Size and other properties of oat bran flour particles in the drink are important for at least two reasons: palatability and physical suspension stability. Depending on their physical and chemical nature suspensions settle slower or quicker, that is, their aqueous and particulate components separate over time to form an upper aqueous phase and a lower particulate phase. Physical stability of a suspension can be defined as the delay of sedimentation caused by suspension stabilizing agents such as soluble β-glucan. Physical stability is visualized as phase separation. It can be monitored by recording the position of the phase separation boundary.

Palatability or feeling of smoothness on ingestion improves with diminishing particle size but is also influenced by the viscosity of the suspension medium, the hardness and form of the particles, and their concentration. Palatability and/or feeling of smoothness improves with increasing viscosity and deteriorates with increasing hardness/angularity and concentration of the particles. An average critical size for particles in suspension is about 25 μm (Tyle P. *Effect of size, shape and hardness of particles in suspension on oral texture and palatability*. Acta Physiologica 84 (1993) 111-118). Food comprising particles of this size and larger, in particular hard and/or angular particles, will not be felt smooth by the average consumer.

It is however difficult and costly to mill oat bran to a particle size at which properties other than size do no longer influence palatability, that is, to a size making the drink feel feeling perfectly smooth on ingestion independent of the nature of the particles.

Another problem with known oat drinks is their tendency to physically disintegrate at storage, during which the particles settle at the bottom of the container holding the drink and a supernatant aqueous phase devoid of particles is formed. While particles can be re-suspended in the aqueous phase by vigorous agitation, this is cumbersome to some consumers, narrows the choice of suitable containers for packaging the drink, and requires the provision of a void at the top of the container not occupied by the drink.

There exists thus a need for improving oat drinks of the aforementioned kind.

OBJECTS OF THE INVENTION

An object of the invention is to provide a method of preparing from an oat raw material comprising arabinoxylan, such as from oat bran, whole groat meal, rolled oats groats or oat endosperm flour, a liquid oat base of improved smoothness.

Another object of the invention is that the improvement in respect of smoothness is not obtained by taking recourse to an oat raw material comprising arabinoxylan, in particular oat bran or a material rich in oat bran, milled to a particle size at which properties other than size do no longer influence palatability.

A further object of the invention is to provide a corresponding liquid oat base.

A still further object of the invention is to provide the liquid oat base of the invention with a desired viscosity, such as one identical with or similar to that of a corresponding not improved liquid oat base.

Additional objects of the invention will become apparent from the following short summary of the invention, the description of a preferred embodiment thereof illustrated in a drawing, and the appended claims.

SUMMARY OF THE INVENTION

In this application "β-glucan, β-glucanase, arabinoxylan, xylanase, α-amylase, β-amylase, protein" is not distinguished from "β-glucans, β-glucanases, arabinoxylans, xylanases, α-amylases, β-amylases, proteins". In this application "liquid" refers to an aqueous liquid which may contain particles suspended therein.

According to the present invention is provided a method of preparing a liquid oat base for use in the manufacture of food for human consumption, the method comprising:
(a) providing a material comprising oat bran comprising from 1% by weight to 50% by weight of β-glucan;
(b) suspending the material comprising oat bran in an aqueous media, in particular water, to form an aqueous suspension;
(c) contacting, in no particular order, said aqueous suspension with α-amylase, β-amylase, β-glucanase, xylanase to raise the concentration of soluble arabinoxylan in the suspension by a factor of 5 or more provide a liquid oat base;

(d) optionally homogenizing the liquid oat base of step (c) to provide homogenized liquid oat base;
(e) optionally destroying enzymatic activity in the liquid oat base of step (c) or the homogenized liquid oat base of step (d) to provide enzymatically inactive liquid oat base;
(f) optionally aseptically packaging the liquid oat base of step (c) or the homogenized liquid oat base of step (d) or the enzymatically inactive liquid oat base of step (e) in a container.

According to a first preferred aspect of the invention step (c) comprises contacting the aqueous suspension of step (b) first with α-amylase, β-amylase, β-glucanase to partially hydrolyze starch and β-glucan, then with xylanase to raise the concentration of soluble arabinoxylan in the suspension by a factor of 5 or more to provide a liquid oat base.

A preferred temperature for α-amylase, β-amylase, β-glucanase contact is from 30° C. to 70° C.

A preferred temperature for xylanase contact is from 40° C. to 70° C., in particular of from 40° C. to 65° C., most preferred of about 60° C.

A preferred material comprises oat bran comprising 1% by weight to 25% by weight of β-glucan.

It is preferred for the material comprising oat bran to be selected from the group consisting of oat bran, whole groat meal (whole meal), rolled oats groats and oat endosperm.

It is furthermore preferred for the material comprising oat bran to comprise or to substantially consist of oat bran particles of a size of 25 μm or higher.

According to a second preferred aspect of the invention is provided a powderous composition for production of liquid oat base of the invention from a material comprising oat bran, the powderous composition comprising or consisting of a material comprising oat bran, α-amylase, β-amylase, β-glucanase, xylanase.

The powderous composition comprising or substantially consisting of a material comprising oat bran, α-amylase, β-amylase, β-glucanase, xylanase can be used in a method of preparing liquid oat base of the invention for use in the manufacture of food for human consumption, the method comprising:
(a) providing said powderous composition;
(b) suspending the powderous composition in an aqueous media, in particular water, to form an aqueous suspension;
(c) raising the temperature of the aqueous suspension to from 40° C. to 70° C. for a time sufficient to degrade starch, β-glucan, and xylan to form liquid oat base;
(d) optionally homogenizing the liquid oat base of step (c) to provide homogenized liquid oat base;
(e) optionally destroying enzymatic activity in the liquid oat base of step (c) or the homogenized liquid oat base of step (d) to provide enzymatically inactive liquid oat base;
(f) optionally aseptically packaging the liquid oat base of step (c) or the homogenized liquid oat base of step (d) or the enzymatically inactive liquid oat base of step (e) in a container.

The material comprising oat bran particles, such as oat bran, whole groat meal (whole meal), rolled oats groats or oat endosperm, provided as a starting material in step (a) comprises or substantially consists, that is, consists to 80% by weight or more, in particular to 90% or 95% by weight or more of particles of a size of 25 μm or higher. A particle "of a size of 25 μm or higher" has an average diameter of 25 μm or higher.

In the method of the invention 80% or more of β-glucan dissolved in the aqueous suspension is degraded by β-glucanase to β-glucan of a molecular weight of from 20,000 D to 400,000 D.

The liquid oat base of the invention is intended for human consumption as such or as an additive or ingredient to other food products. It can be added as such to other food products or in form of a dried powder thereof, in particular in form of a spray dried powder, that is, a powderous oat base.

According to a first preferred aspect, the method of the invention does not affect, i.e. preserves, the content of soluble β-glucan. The preservation of soluble β-glucan is independent of xylanase concentration. Neither does the method of the invention affect the composition of soluble protein, as evidenced by SDS-PAGE gel electrophoresis.

A preferred xylanase of the invention is endo-1,4-β-xylanase. A preferred xylanase concentration is 1250 FXU per 100 g flour but other concentrations, such as from 100 FXU per 100 g floor to 5000 FXU or more per 100 g flour can be employed. One FXU is the amount of endo-1,4-β-xylanase that liberates 7.8 mM of reducing sugars (xylose equivalents) per min from azo-wheat arabinoxylan at pH 6.0 and 50° C.

A preferred temperature of contacting the aqueous suspension of a material comprising oat bran particles with any of α-amylase, β-amylase, β-glucanase is a temperature from 30° C. to 70° C., in particular of from 55° C. to 65° C., most preferred of about 60° C.

According to a further preferred aspect of the invention, contacting the aqueous suspension of a material comprising oat bran particles with xylanase does not affect the viscosity thereof or does affect it only moderately, such as by increasing the viscosity by up to 5% or by up to 10% or by up to 20%. A preferred temperature for xylanase contact is a temperature above room temperature, such as a temperature of 40° C. to 70° C., in particular of from 40° C. to 65° C., most preferred of about 60° C.

According to a another preferred aspect the method of the invention preserves the organoleptic properties of the aqueous suspension of a material rich in oat bran, or even improves them moderately.

According to still another preferred aspect, the method of the invention renders a product of superior physical stability in respect of the starting material aqueous suspension of a material comprising oat bran, such as a product exhibiting phase separation at 20° C. (room temperature) delayed by up to 20% or up to 50% or even by up to 90% and up to 100% or more. While the liquid oat base of the invention is not fully physically stable when stored at room temperature, it disintegrates or settles into an upper aqueous phase and a lower particulate phase substantially slower than a corresponding prior art liquid oat base. A "corresponding prior art liquid oat base" is a known oat base differing from the liquid oat base of the invention at least by not having been incubated with xylanase. Stabilization according to the invention is not obtained by and independent of the addition of suspension stabilizing agent(s), such as hydroxypropyl methyl cellulose (HPMC) or alginate.

The physical stability of the product of the invention can be further improved by homogenization, in particular by high pressure homogenization at a pressure of 150/30 bar or more.

According to an additional preferred aspect a preferred product of the invention, while having an average particle size of about 140 to 225 μm, in particular of about 170 μm, that is, well above the grittiness threshold of 25 μm, does not feel gritty. This is believed to be due to a "rounding" or curling effect of the enzymatic treatment influencing the perception of grittiness and/or to a lowered stiffness or strength of the particles. "Grittiness threshold" is the particle size threshold at which a particulate aqueous suspension feels gritty in the mouth during ingestion.

According to the invention is disclosed an improved liquid oat base, the improvement consisting in one or more of: improved physical stability, improved organoleptic properties, decreased or absent perception of grittiness. Furthermore is disclosed a dry powderous oat base prepared by spray drying of the liquid oat base of the invention or by any other suitable drying method. The liquid oat base of the invention can be reconstituted by suspending the powderous oat base in water or an aqueous solvent. The powderous oat base can also be used as a food additive. Also disclosed is a food product comprising liquid and/or powderous oat base.

In particular is provided a range of food products of various kind comprising the oat base of the invention. These products comprise but are not limited to an oat bran based drink, a whole oats based drink, a fruit flavored drink comprising the oat base of the invention and fruit concentrate, and a high fiber drinking yogurt comprising oat base of the invention and cow milk fermented with a bacterial culture.

The improvement by the method of the invention and of the corresponding product is obtained while substantially conserving the content of water soluble β-glucan of the starting material. In this context, "substantially" means preservation of 75% by weight or more, such as 80% by weight or more and even 90% or 95% by weight or more.

The invention will be now be described in more detail by reference to a number of preferred embodiments and a drawing comprising three figures.

DESCRIPTION OF PREFERRED EMBODIMENTS

Materials and Methods

Oat raw material. Oat bran, whole groat meal (whole meal), rolled oats groats and oat endosperm flour containing from 1% by weight to 50% by weight of β-glucan, about from 8% by weight to 26% by weight of total dietary fiber, from 10% by weight to 22% by weight of protein and from 5% by weight to 15% by weight of fat.

Endo (1-4)β-xylanase. Xylanase Pentopan Mono BG was procured from Novozymes A/S, Denmark. By analysis it was established that the enzyme did not possess β-glucanase activity. The enzyme (UB No. 3.2.1.8; CAS 9025-57-4) is produced by heterogeneous expression of *Thermocytes lanuginosus* in *Aspergillus oryzae*. It is a GH-11 family xylanase with a reported activity of from 2500 XU/W-g to >60000 XU/W-g at 40° C.

Determination of β-glucanase activity. The assay was performed using β-glucazyme tablets from Megazyme International Ireland Ltd. by following the procedure provided by the supplier. The tablets were added to the enzyme solution in sodium acetate buffer (25 mM, pH 4.5) at 40° C. and the solution kept at this temperature for 10 min. The reaction was stopped by adding 6 ml of Trizma buffer (2% w/w, pH 8.5). Samples for analysis were centrifuged for 10 min at 2250 rpm. The absorbance of the supernatant was read at 590 nm.

State-of-the-art liquid oat base (oat drink). A state-of-the-art oat base drink was prepared by adding dry commercial preparations of α-amylase and β-amylase in amounts sufficient to degrade the starch to maltose and maltodextrin. The drink was used as a starting material in experiments carried out for reasons of comparison.

Liquid oat base of the invention. In addition to the use of α-amylase and β-amylase in the preparation of the liquid oat base of the invention β-glucanase is used for degrading most or at least 75% by weight and even more than 80% by weight or 90% by weight of water soluble β-glucan of the starting material, which has a molecular weight of about 1,000,000 D to about 2,000,000 D, to water soluble β-glucan having a molecular weight of from about 20,000 D, in particular from about 50,000 D to about 400,000 D. The suspension of the starting material contained about 10% by weight of material rich in oat bran in water of about 60° C. After incubation for 1 h under stirring at this temperature the so produced liquid oat bran base had a pH of 6.4-6.6 and a viscosity of about 25 cP to 250 cP at 22° C. If desired, the process can be modified to obtain a product of higher or lower viscosity. This oat bran base of the invention was used in the following experiments.

Estimation of soluble arabinoxylan release. The content of soluble arabinoxylan was determined according to the phloroglucinol method of Rose and Inglett, J Food Anal Meth 2; 1 (2010) 66-72. A 200 µl aliquot of the oat suspension supernatant was mixed with 1 ml of reagent. The reagent consists of glacial acetic acid, concentrated hydrochloric acid, 20% (w/v) phloroglucinol in ethanol, and 1.75% (w/v) glucose in a proportion of 110:2:5:1. Samples were incubated at 100° C. for 25 min. After cooling to room temperature the absorbance was read at 552 nm and 510 nm. Quantification of the content of soluble arabinoxylan was obtained relating the measured absorbance to that of a calibration curve constructed by using D(+)xylose. The results are expressed as mM of xylose equivalents (XE).

Determination of β-glucan content. The method was developed using the Mixed-Linkage β-glucan assay kit from Megazyme International Ireland Ltd. The procedure described by the supplier was slightly modified. One gram of oat bran based drink, 200 µl of ethanol (50% v/v) and 4 ml of phosphate buffer (20 mM, pH 6.5) was added to each test tube. The tubes were vortex mixed and placed in boiling water for 2 min, then transferred to a water bath at 50° C. and kept there for 5 minutes. After adding 200 µl of an aqueous solution of lichenase enzyme (10 U) to each test tube the samples were stored in the water bath for 1 h. Sodium acetate buffer (5 ml, 200 mM, pH 4) was added to each tube. The tubes were centrifuged at 1000 rpm for 15 min. One hundred µL of the supernatant were mixed with 100 µl of the β-glucosidase enzyme (0.2 U) solution. A blank was prepared for each sample (no addition of β-glucosidase; addition of 100 µl of sodium acetate buffer (50 mM, pH 4)).

Samples were incubated in a water bath at 50° C. for 15 min. A glucose standard was also analyzed. Three ml of GODOP reagent (potassium phosphate buffer (1 mM, pH 7.4), p-hydroxybenzoic acid (0.22 M) and sodium azide (0.4% w/w) was added to each tube. The tubes were then incubated for further 20 min at 50° C. The absorbance was read at 510 nm within 1 h.

SDS-PAGE Gel Electrophoresis. To establish whether protein extracted after application of the enzyme differ from original protein a gel electrophoresis was performed at three different xylanase concentrations. It was shown that xylanase treatment does not affect the molecular weight distribution nor the composition of the proteins.

Particle size measurement. Particle size measurement was performed by laser beam diffraction using a Mastersizer 2000, Hydro 2000SM instrument (Malvern Instruments, Worcestershire, UK). The particle size distribution recorded by this technique is volume based and reported in a graph showing the volume percentage of particles of a given size. The particle size determination is based on the assumption that the particles are spherical and homogeneous and that the optical properties of the medium are known. For particles of same kind, such as in the present context, the method is believed to render reliable results.

EXAMPLE 1. β-Glucan content of oat bran base of the invention in relation to amount of xylanase used for its production. The state-of-the-art oat bran based drink described above was incubated at 40° C. for 15 min with different amounts of xylanase. The product was analyzed for β-glucan concentration. The results are shown in Table 1.

TABLE 1

β-Glucan content of oat bran base samples treated with different amounts of xylanase at 40° C. for 15 min

| Xylanase FXU/100 g OBF (Oat Bran) | β-glucan (% by weight) |
|---|---|
| 0 | 1.3 |
| 100 | 1.4 |
| 1000 | 1.5 |
| 2000 | 1.4 |

EXAMPLE 2. Physical stability of the improved liquid oat base of the invention. Physical stability was determined by measuring phase separation upon storing in a glass vial a sample of the improved liquid oat base for a given period of time at a selected temperature. During storage an upper clear liquid phase appeared. It increased in height until a stable end point state was reached at which the height of the lower particulate phase remained stable. Physical stability index $I_{phs}$ at time $t_{ts}$ is conveniently expressed as 100× the ratio of upper phase height at $t_s$ to upper phase height at end point (storage for indefinite period) at which sedimentation equilibrium has been reached.

A decreased separation rate is indicative of improved physical stability. Homogenized samples of the aqueous oat base of the invention and the prior art aqueous oat base not treated with xylanase were stored in test tubes at 4° C. Phase separation (upper aqueous phase; lower particulate phase) was measured at 2, 24, 36 and 48 hours from homogenization (Table 2). Physical stability

TABLE 2

Physical stability, 1 h enzymatic treatment with xylanase at 40° C.

| Xylanase conc. | Physical stability index $I_{phs}$* | | | |
|---|---|---|---|---|
| FXU/100 g OBF | 2 h | 24 h | 36 h | 48 h |
| 0 | 67 | 47 | 40 | 33 |
| 100 | 92 | 82 | 63 | 55 |
| 1000 | 97 | 82 | 83 | 75 |
| 2000 | 98 | 92 | 83 | 78 |

*100% = no phase separation; 0% = complete phase separation

About 50% of the increase in physical stability is achieved after a reaction time of merely 5 min (Table 3).

TABLE 3

Increase in physical stability (physical stability index $I_{phs}$) in respect of length of enzymatic treatment at 40° C., xylanase conc. 1000 FXU/100 g OBF

| | Reaction time, min | | | | | | |
|---|---|---|---|---|---|---|---|
| Storage time, h | 0 | 5 | 10 | 15 | 20 | 25 | 30 |
| 2 | 67 | 97 | 98 | 95 | 95 | 95 | 98 |
| 24 | 47 | 97 | 97 | 93 | 95 | 93 | 93 |

EXAMPLE 3. Effect of xylanase concentration on the content of soluble arabinoxylan. Soluble arabinoxylan content was measured after incubation at 40° C. of samples at different xylanase concentrations. The results are shown in Table 4 expressed as xylose equivalents.

TABLE 4

Xylose equivalents (XE) in samples treated with different concentrations of xylanase (w/v) for 60 min

| Xylanase (FXU/100 g OBF) | XE (mM) |
|---|---|
| 0 | 0.38 |
| 100 | 7.4 |
| 1000 | 15.0 |
| 2000 | 14.0 |

EXAMPLE 4. Particle size measurement. To establish whether the enzyme degrades cell walls and thus reduces particle size, the size of liquid oat bran base particles of the invention produced at different xylanase concentrations was measured. Control samples were not incubated with xylanase. A significant decrease in particle size was observed upon treatment with xylanase (1 h at 40° C.). Table 5 shows the mean particle diameter determined from the particle volume weight of xylanase treated samples.

TABLE 5

Volume weight diameter of oat bran drink samples after xylanase treatment

| Xylanase (FXU/100 g) | Mean diameter (μm) | Decrease (%) |
|---|---|---|
| 0 | 307 | — |
| 100 | 207 | 32.6 |
| 1000 | 184 | 40.0 |
| 2000 | 154 | 49.8 |

EXAMPLE 5. Effect of reaction time on soluble arabinoxylan content. Soluble arabinoxylan content was measured after the incubation of the samples for different time periods. This assay was performed to assess changes in the concentration of arabinoxylan degradation products during the reaction. Table 6 shows that there was a significant increase in arabinoxylan concentration after a reaction time of 5 min. A further, slight increase was observed at longer reaction times.

TABLE 6

Content of soluble arabinoxylan in samples treated with xylanase (1000 FXU/100 g OBF) for different reaction times

| Reaction time, min | | | | | | | | | | |
|---|---|---|---|---|---|---|---|---|---|---|
| | 0 | 5 | 10 | 15 | 20 | 25 | 30 | 35 | 40 | 50 |
| Xylose equivalents, mM | 0.5 | 7.7 | 8.2 | 9.6 | 8.3 | 9.1 | 8.9 | 11.1 | 10.7 | 11.4 |

EXAMPLE 6. Effect of reaction temperature. An incubation time of 15 min was chosen since had been shown above to provide good physical stability and a substantial increase of soluble arabinoxylan. The effect of temperature variation on enzymatic degradation by xylanase was analyzed to find an optimum reaction temperature.

Oat bran based drink was incubated with xylanase 1000 FXU/100 g OBF for 15 min at 40° C., 50° C., and 60° C. (Table 7).

TABLE 7

Physical stability at 4° C. of xylanase treated oat bran based drink

| Xylanase, 15 min | Physical stability index $I_{phs}$, 4° C., % | | |
|---|---|---|---|
| at ° C. | 2 h | 24 h | 72 h |
| No xylanase | 58 | 42 | 37 |
| 40 | 100 | 97 | 88 |
| 50 | 100 | 93 | 82 |
| 60 | 100 | 97 | 97 |

Figure 1:
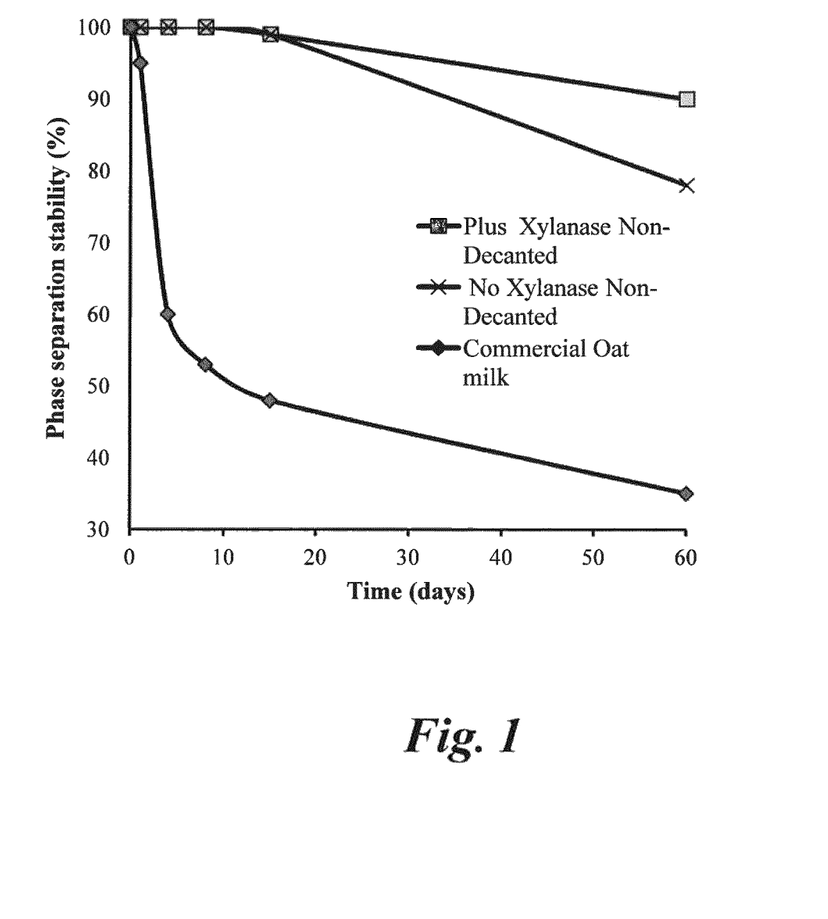
FIG. 1 is a graph illustrating the effect of high pressure homogenization on liquid oat bran base of the invention containing all fiber present in the starting material and on a prior art decanted oat bran base from which such insoluble fiber has been removed by decantation.
Figure 2:
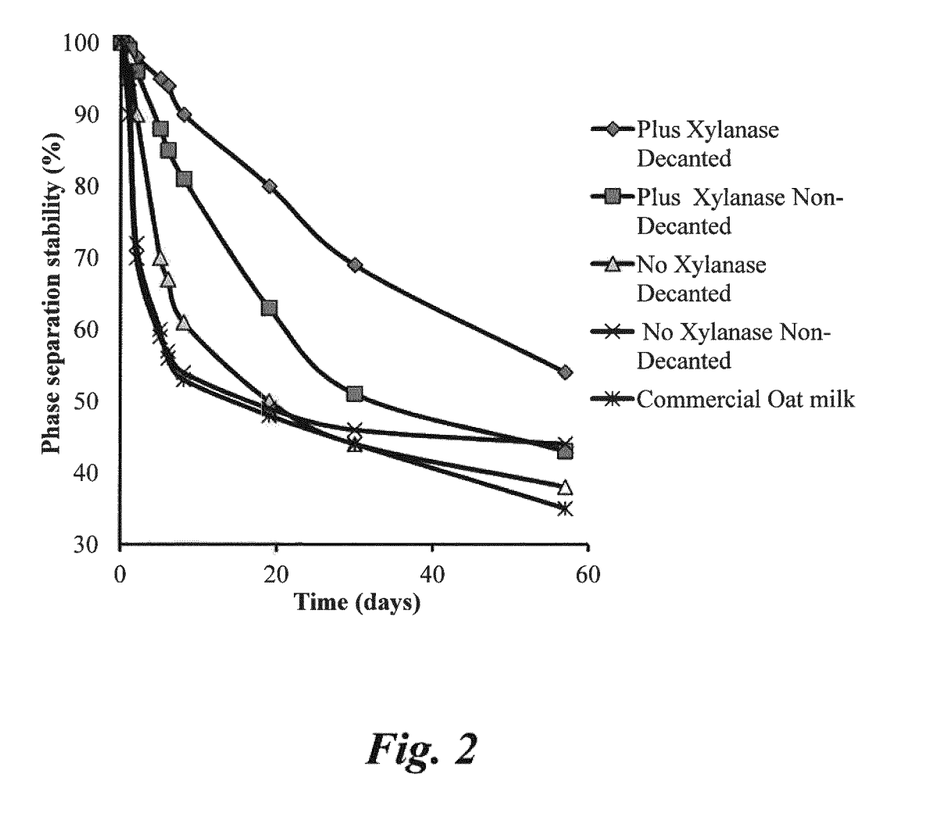
FIG. 2 is a graph illustrating the effect of high pressure homogenization on whole oat liquid oat base of the invention and on a prior art decanted oat bran base from which such insoluble fiber has been removed by decantation.

EXAMPLE 7. Homogenization. The physical storage stability of the liquid oat base of the invention can be further improved by homogenization. Performing homogenization in a two-step homogenizer providing a pressure of at least 150/30 bar the product shows improved physical stability even in the presence of insoluble fibers, that is, prior to decantation by which insoluble fibers are removed. Improved stability of the liquid oat base of the invention produced from whole oat (FIG. 1) and from oat bran (FIG. 2) over that of a commercial oat base (oat drink) is demonstrated in the Figures.

EXAMPLE 8. Content of soluble arabinoxylan in oat bran based drink treated with xylanase at various temperatures. The known oat bran base (oat drink) described above was incubated for 15 min with 1000 FXU/100 g OBF of xylanase at 40° C., 50° C., and 60° C. The content of soluble arabinoxylan was found to have been increased at all temperatures by a factor of 5 or more (Table 8).

TABLE 8

Soluble arabinoxylan content of xylanase treated oat bran based drink

| Xylanase for 15 min; ° C. | none | 40 | 50 | 60 |
|---|---|---|---|---|
| Xylose equivalents, mM | 0.89 | 6.6 | 8.7 | 8.1 |

Figure 3:
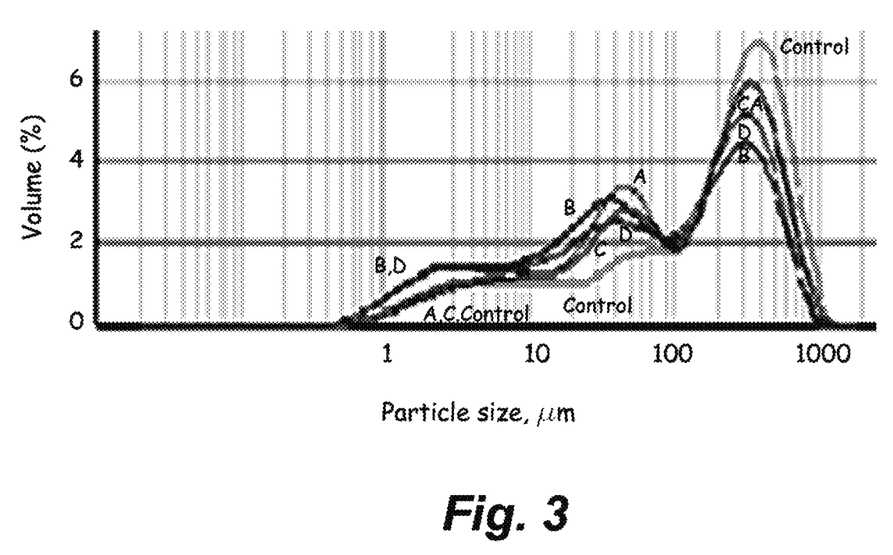
FIG. 3 is a graph illustrating the particle size distribution of homogenized and not homogenized oat bran base of the invention as well as of a prior art control.

EXAMPLE 9. Particle size distribution. FIG. 3 shows the distribution of particle size of homogenized and non-homogenized oat bran base of the invention. In Table 10 corresponding volume weight diameter data are given for the following samples:

For evaluating the effect of homogenization five samples were prepared: Control: Non-homogenized oat bran base not treated with xylanase;
   Sample A: Non-homogenized; 1000 FXU xylanase per 100 g OBF; xylanase 15 min at 60° C.;
   Sample B: Homogenized for 2 min; 1000 FXU xylanase per 100 g OBF; xylanase 15 min at 60° C.;
   Sample C: Non-homogenized, 500 FXU xylanase per 100 g OBF; xylanase 30 min at 60° C.;
   Sample D: Homogenized for 2 min, 500 FXU xylanase per 100 g OBF; xylanase 30 min at 60° C.

TABLE 9

Diameter of samples A through D and of control determined from their volume weight

| Sample | Diameter, μm | Decrease (%) |
|---|---|---|
| Control | 272 | 0 |
| A | 207 | 24.0 |
| B | 159 | 41.7 |
| C | 216 | 20.5 |
| D | 173 | 36.4 |

As evident from Table 9 particle size reduction is more pronounced at the higher enzyme concentration.

EXAMPLE 10. Preparation of oat bran drink. A beta-glucan rich (15% w/w) oat bran drink according to the invention was prepared by suspending from 7% by weight to 15% by weight of oat bran flour/enzyme mix in water. The suspension was incubated at 55° C. to 65° C. under agitation for from about 30 min to about 2 h. Incubation was stopped by heating, in particular to at least 80° C. or even 100° C. or more. The suspension was UHT treated, homogenized at a pressure of 150/30 bar, and cooled to 4° C. After storage for 20 days at 4° C. the preparation showed no significant (5% or more) phase separation. No additives had been added to the so prepared oat bran drink of the invention to stabilize it against phase separation. Alternatively the oat bran drink of the invention prepared in this manner can be pasteurized.

EXAMPLE 11. Dried oat bran drink. Oat bran drink of Example 11 was dried to a white powder by spray drying using equipment for spray drying cow milk. The powder can be used for reconstitution of the drink by suspending it in water or as a food additive.

EXAMPLE 12. Preparation of a whole grain oat drink. The procedure followed was essentially that of Example 10 except for that whole grain oat flour was used as starting material.

EXAMPLE 13. Dried whole oat grain drink. Whole grain oat drink of Example 12 was dried to a white powder by spray drying using equipment for spray drying cow milk. The powder can be used for reconstitution of the drink by suspending it in water or as food additive.

EXAMPLE 14. Preparation of a fruit flavored drink comprising oat bran drink. Several samples were prepared by mixing from 25% (w/w) to 95% (w/w) of oat bran drink of Example 10 or reconstituted drink according to Example 11 with fruit concentrate of desired flavor. The mixtures were cooled to 4° C. and bottled under aseptic conditions. The drinks proved to be stable for three weeks at this temperature in absence of any stabilizing food additives.

EXAMPLE 15. Preparation of a fruit flavored drink comprising whole grain oat drink. Several samples were prepared by mixing from 25% (w/w) to 95% (w/w) of whole grain oat drink of Example 12 or reconstituted drink according to Example 13 with fruit concentrate of desired flavor. The mixtures were cooled to 4° C. and bottled under aseptic conditions. The drinks proved to be stable for three weeks at this temperature in absence of any stabilizing food additives.

EXAMPLE 16. Preparation of a nutritious high fiber drinking yogurt based on fermented oat bran drink and cow milk. From 50% by weight to 95% or more by weight (several samples prepared) of the oat bran drink of Example 10 or such drink reconstituted according to Example 11 were mixed with standard cow milk. The mixture was passed through a heat exchanger. The mixture was pasteurized and subsequently cooled to about 40° C. to about 50° C. followed by inoculation with the required quantity of desired bacterial culture. The culture may optionally comprise probiotic strains. The blend was thoroughly mixed and fermented until it reached a pH of about 4.5. The fermented product can be flavored with spices to provide a savory type of drinking yoghurt or a fruit flavored drinking yoghurt by adding a fruit concentrate of desired flavor under aseptic conditions. The drinking yoghurt is then bottled under aseptic conditions and stored at +4° C. The drinking yoghurt proved to be stable for three weeks at this temperature in absence of any stabilizing food additives.

What is claimed is:

1. A method of preparing a liquid oat base for use in the manufacture of food for human consumption, comprising:
   (a) providing an oat bran material including from 1% to 50% by weight of β-glucan;
   (b) suspending the oat bran material in an aqueous media, to form an aqueous suspension;
   (c) contacting, in no particular order, the aqueous suspension with a mixture of enzymes consisting of α-amylase, β-amylase, β-glucanase, and xylanase for a period of at least about five minutes to raise the concentration of soluble arabinoxylan in the suspension by a factor of 5 or more to provide a liquid oat base;
   (d) homogenizing the liquid oat base of step (c) in a first homogenization step at a pressure of at least about 150 bar to provide homogenized liquid oat base;
   (e) optionally destroying enzymatic activity in the homogenized liquid oat base of step (d) to provide enzymatically inactive liquid oat base; and
   (f) optionally aseptically packaging the homogenized liquid oat base of step (d) or the enzymatically inactive liquid oat base of step (e) in a container;
   whereby the resulting liquid oat base contains oat bran particles which have an average particle size of at least 50 μm.

2. The method of claim 1, wherein step (c) further comprises contacting the aqueous suspension of step (b) first with the α-amylase, β-amylase, and β-glucanase to partially hydrolyze starch and β-glucan, then with the xylanase to raise the concentration of soluble arabinoxylan in the suspension by a factor of 5 or more to provide a liquid oat base.

3. The method of claim 1, wherein the temperature for the α-amylase, β-amylase, and β-glucanase contact is from 30° C. to 70° C.

4. The method of claim 1, wherein the temperature for the xylanase contact is from 40° C. to 70° C.

5. The method of claim 1, wherein the oat bran material is selected from the group consisting of oat bran, whole groat meal (whole meal), rolled oats groats and oat endosperm.

6. The method of claim 1, wherein the xylanase is an endo-1,4-β-xylanase.

7. The method of claim 1, wherein 80% or more of β-glucan dissolved in the aqueous suspension is degraded by β-glucanase to β-glucan of a molecular weight ranging from 20,000 D to 400,000 D.

8. The method of claim 1, wherein the aqueous suspension is water.

9. A method of preparing a liquid oat base for use in the manufacture of food for human consumption, comprising:
   (a) providing a powderous composition consisting of oat bran material, α-amylase, β-amylase, β-glucanase, and xylanase;
   (b) suspending the powderous composition in an aqueous media to form an aqueous suspension;
   (c) raising the temperature of the aqueous suspension from 40° C. to 70° C. for a time sufficient to degrade starch, β-glucan, and xylan to form liquid oat base; wherein said α-amylase, β-amylase, β-glucanase, and xylanase are allowed to act for at least about five minutes;
   (d) homogenizing the liquid oat base of step (c) in a first homogenization step at a pressure of at least about 150 bar to provide homogenized liquid oat base;
   (e) optionally destroying enzymatic activity in the homogenized liquid oat base of step (d) to provide enzymatically inactive liquid oat base; and
   (f) optionally aseptically packaging in a container the homogenized liquid oat base of step (d) or the enzymatically inactive liquid oat base of step (e);
   wherein the resulting liquid oat base contains oat bran particles which have an average particle size of at least 50 μm.

10. The method of claim 9, wherein the media suspension is water.

11. The method of claim 1, wherein the homogenizing the liquid oat base of the step (c) is carried out using a two-step homogenizer wherein a first homogenization step is carried out at a pressure of at least about 150 bar and a second homogenization step is carried out at a pressure of at least about 30 bar.

12. The method of claim 9, wherein the homogenizing the liquid oat base of the step (c) is carried out using a two-step homogenizer wherein a first homogenization step is carried out at a pressure of at least about 150 bar and a second homogenization step is carried out at a pressure of at least about 30 bar.

13. The method of claim 1, wherein the oat bran particles have an average particle size of between 50 μm and 1000 μm.

14. The method of claim 1, where in the oat bran particles have an average particle size of between 140 μm and 225 μm.

15. The method of claim 9, wherein the oat bran particles have an average particle size of between 50 μm and 1000 μm.

16. The method of claim 9, where in the oat bran particles have an average particle size of between 140 μm and 225 μm.

17. The method of claim 1, wherein the oat bran material has a first total particle content and the homogenized liquid oat base has a second total particle content, wherein the first total particle content is equal to the second total particle content.

18. The method of claim 9, wherein the oat bran material has a first total particle content and the homogenized liquid oat base has a second total particle content, wherein the first total particle content is equal to the second total particle content.

19. The method of claim 1 wherein the treatment time is between five minutes and thirty minutes.

\* \* \* \* \*